United States Patent
Weckström

(12) 
(10) Patent No.: US 7,353,689 B2
(45) Date of Patent: Apr. 8, 2008

(54) LIQUID SEPARATOR FOR A GAS ANALYZER AND METHOD FOR SEPARATING A LIQUID COMPONENT FROM GAS

(75) Inventor: Kurt Weckström, Espoo (FI)

(73) Assignee: GE Healthcare Finland Oy, Helsinki (FI)

( * ) Notice: Subject to any disclaimer, the term of this patent is extended or adjusted under 35 U.S.C. 154(b) by 203 days.

(21) Appl. No.: 10/780,123

(22) Filed: Feb. 17, 2004

(65) Prior Publication Data

US 2005/0178269 A1    Aug. 18, 2005

(51) Int. Cl.
*G01N 1/22*    (2006.01)
(52) U.S. Cl. .......... 73/19.12; 73/19.01; 95/46
(58) Field of Classification Search .......... 73/31.07, 73/19.01, 19.12; 210/640, 321.6, 321.87, 210/321.72, 321.75, 321.84; 95/46, 45; 96/6
See application file for complete search history.

(56) References Cited

U.S. PATENT DOCUMENTS

| | | | |
|---|---|---|---|
| 3,772,909 A * | 11/1973 | Anderson | 73/23.41 |
| 3,929,003 A * | 12/1975 | LLewellyn | 73/61.72 |
| 4,304,578 A | 12/1981 | Hakala et al. | |
| 4,382,806 A | 5/1983 | Hakala et al. | |
| 4,509,359 A | 4/1985 | Gedeon et al. | |
| 4,886,528 A * | 12/1989 | Aaltonen et al. | 96/6 |
| 4,894,163 A * | 1/1990 | Watanabe et al. | 210/640 |
| 5,235,843 A * | 8/1993 | Langhorst | 73/19.02 |
| 5,657,750 A | 8/1997 | Colman et al. | |
| 6,054,051 A * | 4/2000 | van Reis | 210/641 |
| 6,110,368 A | 8/2000 | Hopkins et al. | |
| 6,155,097 A * | 12/2000 | Arnold | 73/23.35 |
| 2002/0110924 A1 | 8/2002 | Carr | |

FOREIGN PATENT DOCUMENTS

EP    1 052 013    11/2000

OTHER PUBLICATIONS

EP Search Report dated Sep. 14, 2005.

* cited by examiner

*Primary Examiner*—Hezron Williams
*Assistant Examiner*—Ryan Christensen
(74) *Attorney, Agent, or Firm*—Andrus, Sceales, Starke & Sawall, LLP

(57) ABSTRACT

Liquid separator for a gas analyzer and method for separating a liquid component from gas. The liquid separator comprises an input passage having an input end and an output end, an output passage having an input end and an output end, a wall formed of a gas permeable and liquid impermeable material separating the input passage and the output passage, means for introducing a gas sample containing liquid through the input end into the input passage with a first portion of the gas passing through said wall to the output passage and a second portion of the gas and the liquid remaining in the input passage, a vacuum means for flowing the first portion of the gas through the output end from the output passage to a measuring unit, a first conduit connecting the output end of the input passage and for conducting the second portion of the gas and the liquid furtheron with vacuum means. The output passage is arranged to widen towards the output end of the output passage and/or the input passage is arranged to narrow towards the output end of the input passage.

24 Claims, 3 Drawing Sheets

LIQUID SEPARATOR FOR A GAS ANALYZER AND METHOD FOR SEPARATING A LIQUID COMPONENT FROM GAS

The invention relates to an apparatus and a method for separating a liquid component for example from a patient's exhalation gas to be delivered to a gas analyzer, said apparatus comprising a first passage, wherein the exhalation gas coming from a patient is delivered and wherein the inflowing gas is divided into two components in a manner that some of the gas flows to a gas analyzer and some of the gas, as well as a liquid component possibly entrapped in the exhalation gas is carried away past the analyzer, a second passage, through which a patient's exhalation gas flows from the first passage to the gas analyzer, and a gas permeable wall, which separates these passages and through which the gas flows from first passage to second passage.

BACKGROUND OF THE INVENTION

In anesthesia or in intensive care, the condition of a patient is often monitored e.g. by analyzing the air exhaled by the patient for its carbon dioxide content. Therefore, a small portion of the exhalation air is delivered to a gas analyzer. This sample often carries along to the analyzer some water vapor, which condensates into droplets, and also some dust, mucus and blood. Such components carried along with the sample have a detrimental effect on the gas analyzer and measuring result. This is why the liquid components are often removed and collected from a gas sample upstream of the actual gas analyzer.

In prior known gas analyzers, e.g. U.S. Pat. Nos. 4,304,578 and 4,382,806, water has been removed from a gas sample by using a water separator, provided with a water-separation chamber, which divides the flow into two partial flows in a manner that the main flow is sucked through a measuring sensor by means of a tube connected with the water-separation chamber and a many times smaller side flow is sucked continuously by way of a tube connected with the bottom section of said water-separation chamber into a water receiver for retaining therein the water contained in a gas sample and further on to a pump. However, this solution is not totally sufficient, since some of the liquid components may still find access to the measuring sensor along with the gas sample. The response time of the gas analyzer may also increase because of the internal volume of the water-separation chamber.

It has also been known in the art, e.g. in U.S. Pat. No. 4,509,359, to use a moisture equalizing tube. In this case the analyzer is not usually fitted with an individual water separator but, instead, a sampling tube between a patient and the gas analyzer as well as a tube between a sampling connector in the analyzer and a measuring sensor are made of a material which equalizes moisture of the gas inside the tube to be the same as that on the outside, so that water always tends to find its way towards the drier side, the moisture of the gas sample equalizing to be the same as the moisture of ambient air and no condensation occurs on the tube walls.

This prior art solution has a fast response time but involves some serious drawbacks. The tube material is only capable of a limited transfer of water through the wall per unit time, whereby the water splashed from the tubing of a respirator, a patient's mucus or blood may end up in the measuring sensor. Dust in the air also finds its way to a measuring sensor and causes problems there.

Another improved fluid filtering device is described in U.S. Pat. No. 5,657,750. The upstream end of the sampling tube is provided with a tubular housing containing a hydrophobic hollow fiber filter element. In order not to increase the response time of the gas analyzer the tubular housing must have small volume. It is possible that the device can handle a small amount of water but it is easily obstructed by mucus or blood. The device would then have to be replaced. This may happen quite often in critical care use and would decrease the cost-effectiveness of the device.

In order to overcome the problems described above a special type of water separator was developed and the basic solution is described in U.S. Pat. No. 4,886,528. A passage, wherein a liquid component is separated from a gas flow, is divided into two sections by means of a gas permeable and liquid impermeable material. Thus a sample picked up from the exhalation air of a patient is delivered into the first passage of a water separator, from which the liquid component along with a minor amount of gas is sucked away, usually by way of a water receiver. Most of the gas flow received in the first passage is sucked through the liquid impermeable material into the second passage and further to a gas analyzer. This hydrophobic filter material prevents effectively the passage of liquid to the gas analyzer. In order to reduce flow resistance caused by the liquid impermeable material a certain contact area is necessary. To try to avoid an excessive increase in the response time of the gas analyzer the favored passages are kept narrow and elongated. The maximum cross-section area of a passage would preferably be close to that of the input conduit but in practice it is slightly larger for mechanical reasons. A larger input passage is e.g. less prone to clogging.

The last described solution works well as water separator but it has a major influence on the response time of the gas analyzer. In fact, its contribution to the response time is the most significant compared to the sampling line and the gas sensor with internal tubing. This is a drawback especially for an analyzer with low sample flow e.g. in neonatal gas measurement applications.

SUMMARY OF THE PRESENT INVENTION

An object of the present invention is to provide a liquid separator and a method by means of which the drawbacks of the prior art can be eliminated. This can be achieved by means of the present invention. The invention is based on the idea according to which one or both of the passages in contact with a gas permeable and liquid impermeable filter are tapered in such a manner that the transit time for all measured molecules in a gas mixture are approximately the same independently of their individual paths along the passages. In other words the invention is for example characterized in that the output passage is arranged to widen towards the output end of the output passage.

An advantage of the invention is that the response time of the gas analyzer is only slightly affected by the addition of a separate and well functioning liquid separator. Another advantage is that the solution is simple and easy to apply.

DESCRIPTION OF THE DRAWINGS

In the following, the invention will be described in more detail with reference made to the attached drawings, in which.

DETAILED DESCRIPTION OF THE PREFERRED EMBODIMENTS

Figure 1:
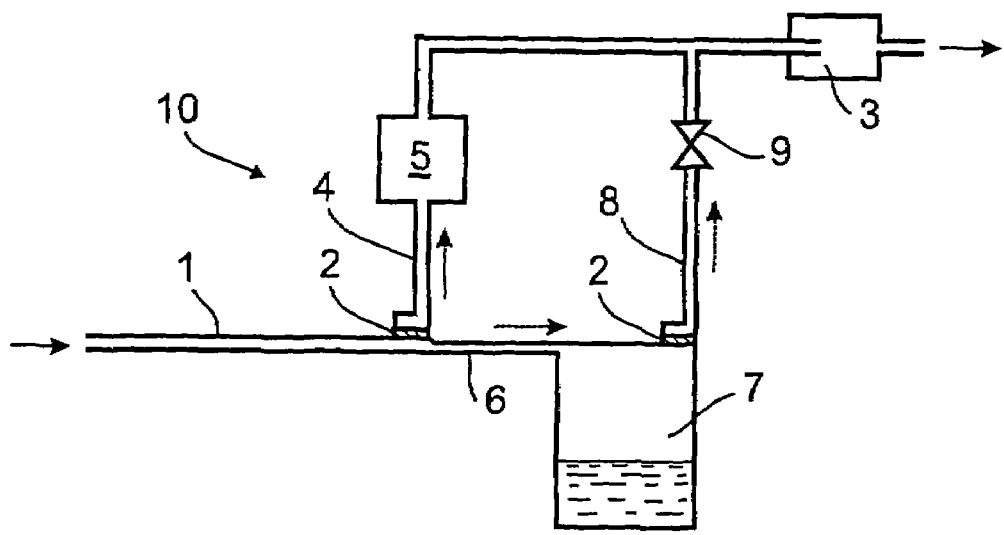
FIG. 1 shows the basic principle of a liquid separator in a gas analyzer.

FIG. 1 shows the basic principle of a liquid separator in a gas analyzer system. With liquid is usually meant water but it could also be any water containing substance like mucus and blood or it could be any liquid for which the liquid separator can be made functional. A gas sample is brought from a patient via a conduit or sample line 1. The gas sample is divided into two partial flows by using a gas permeable and liquid impermeable and often hydrophobic filter 2. The first flow portion is sucked by a vacuum means for example a pump 3 through the filter 2 into a conduit 4 and further to a measuring sensor 5. The second flow portion is sucked by means of a vacuum means for example a pump through a conduit 6 into a liquid receiving means 7. The liquid receiving means 7 is connected to the pump 3 by a conduit 8, which is also provided with a liquid impermeable hydrophobic filter 2, which prevents liquid flow from the liquid receiving means 7 through the conduit 8 to the pump 3. The conduit 8 is equipped with a flow-resisting element 9 upstream of pump 3. In this connection it must be understood that FIG. 1 is only an example. It is quite possible that a liquid separator is equipped with two pumps, i.e. one pump is used for conduit 4 and the other pump is used for conduit 8. It must further be understood that a liquid separator can be materialized also without any liquid receiving means.

Referring back to the flow-resisting element 9 it can be seen that the element can be used for adjusting the mutual relationship between flows occurring through conduits 4 and 8. The flow through conduit 8 is normally much smaller than the measurement flow through conduit 4. Its function is to prevent back-flow from the liquid receiving means 7 into conduit 4. This could disturb the gas mixture and increase the response time of the gas analyzer 10. As an example, if the total input flow in conduit 1 is 200 ml/min, the side flow through conduit 8 could be 25 ml/min, leaving 175 ml/min of gas flow for the gas sensor 5.

Figure 2:
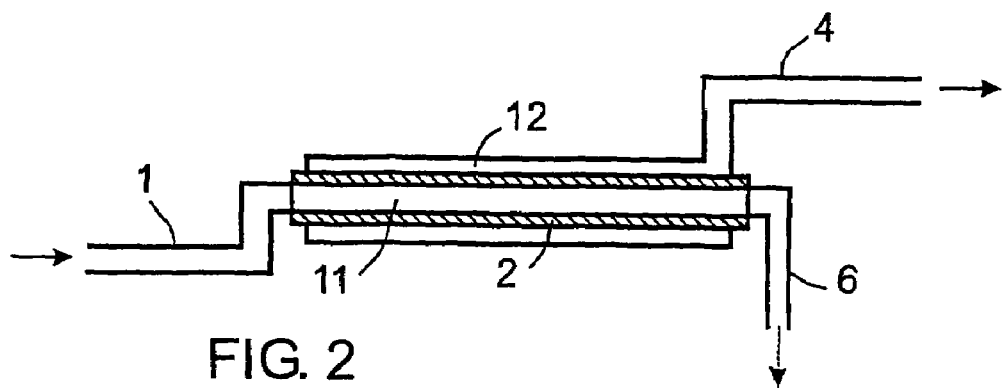
FIG. 2 shows one embodiment of a liquid separator according to the prior art.

In the following description only the part of the liquid separator affecting the response time of the gas sensor 5 will be discussed. This part is shown in FIG. 2. The input conduit 1 is connected to an elongated input passage 11, which ends in the conduit 6 of the liquid receiving means 7. The input passage 11 is surrounded by a gas permeable and liquid impermeable hydrophobic filter 2. Concentric with this filter is the output passage 12, which ends in the conduit 4 with connection to the gas sensor 5. The passages are tubular in order to have large contact surface. This is essential for minimizing the flow resistance through the liquid separator. However, the response time is not optimal as will become evident below.

Figure 3:
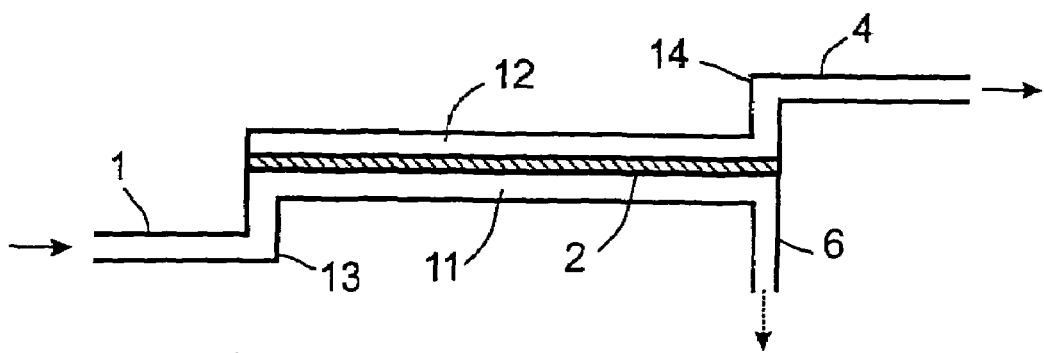
FIG. 3 shows another embodiment of a liquid separator according to the prior art.

Another embodiment according to the prior art is shown in FIG. 3.

The elongated passages are not concentric but they are semi-circular or rectangular in cross-section. The liquid impermeable hydrophobic filter 2 is a flat membrane in between the input passage 11 and the output passage 12, the membrane being a common surface to both passages. In order to save space, the passages may be bent into a loop in the direction of the filter plane. However, such bends will give a contribution to the response time. So will also 90 degrees bends like 13 and 14 in the conduit connections. Such bends cannot always be avoided but the number of bends should be reduced to a minimum. The passages 11 and 12 will give a contribution to the response time of the gas sensor even if they are straight like in FIGS. 2 and 3. This has to do with how fast the gas front is moving through the input passage 11 and further through the hydrophobic filter 2 to the end of output passage 12. What is meant with a gas front is a sudden change in the constituent of the gas to be measured. As the gas front travels along the input passage 11, gradually more of its content is transferred to the output passage 12. It means that the flow velocity in the input passage 11 slows down when going along the passage. In the same manner the velocity of the gas front grows as it flows along the output passage 12. As a consequence, the delay time for the gas front within the passages will be different depending on where the gas molecules went through the filter 2.

The behavior mentioned above is shown graphically in FIG. 4. Two graphs are shown together with the embodiment of FIG. 3. The prior art dimensions are drawn using dashed lines. Dashed lines are also used in the graphs for prior art results. The gas flow through the passages is indicated using dotted lines. Three positions for transfer from the input passage 11 to the output passage 12 through filter 2 are shown with reference to the graphs. The length of the passages 11 and 12 and the active portion of the filter 2 are essentially the same. In a simulation the input passage 11 had a hydraulic diameter of 1.8 mm and the diameter of the output passage 12 was 1.5 mm as can be seen in the upper graph. The hydraulic diameter is the diameter of a cylindrical tube, equivalent in flow sense to a passage with a non-circular cross-section. The actual input passage was rectangular with the dimensions 3×1.5 mm and the output passage 3×1 mm. In the calculations it is easier to use the hydraulic diameter and the results are reliable enough. The passages 11 and 12 were 38 mm long. The calculated flow delay time through the passages is shown in the second graph. The delay time curve has a minimum approximately halfway through the input passage 11. If the gas molecules are sucked through the hydrophobic filter 2 at that point the total delay time of the passages is about 50 ms. The flow value in conduit 1 was 150 ml/min and 20 ml/min in conduit 6. The delay time increases toward the ends of the passages. At the positions indicated it is about 70 ms. If the gas transfer through filter 2 happens at the input end of the passage 11 the delay is almost 100 ms. At the other end the delay is about 85 ms. The reason for this non-symmetry is the small side-flow through conduit 6 to the liquid receiving means 7. The side-flow actually speeds up the transfer time at the end of passage 11 because the flow velocity is higher than without this flow. The simulation was done using conventional flow physics like the Bernoulli's equation and the equations of continuity. The hydrophobic filter 2 was simulated as a large number of small pipes between the input passage 11 and the output passage 12.

The next question is whether one could modify the liquid separator in order to control the delay time of the gas front. Surprisingly, it was possible to almost eliminate the excessive delay time at the input end by tapering the output passage 12 in the upstream direction at the input end 15, i.e. by forming the output passage 12 so that it has a widening profile extending from the input end 15 towards the output end 16 of the output passage 12. This is shown using continuous lines in the embodiment of FIG. 4 and also in the graphs. The tapered portion ends at about half of the passage length but it could also extent differently along the passage according to the demand of the calculation.

Figure 4:
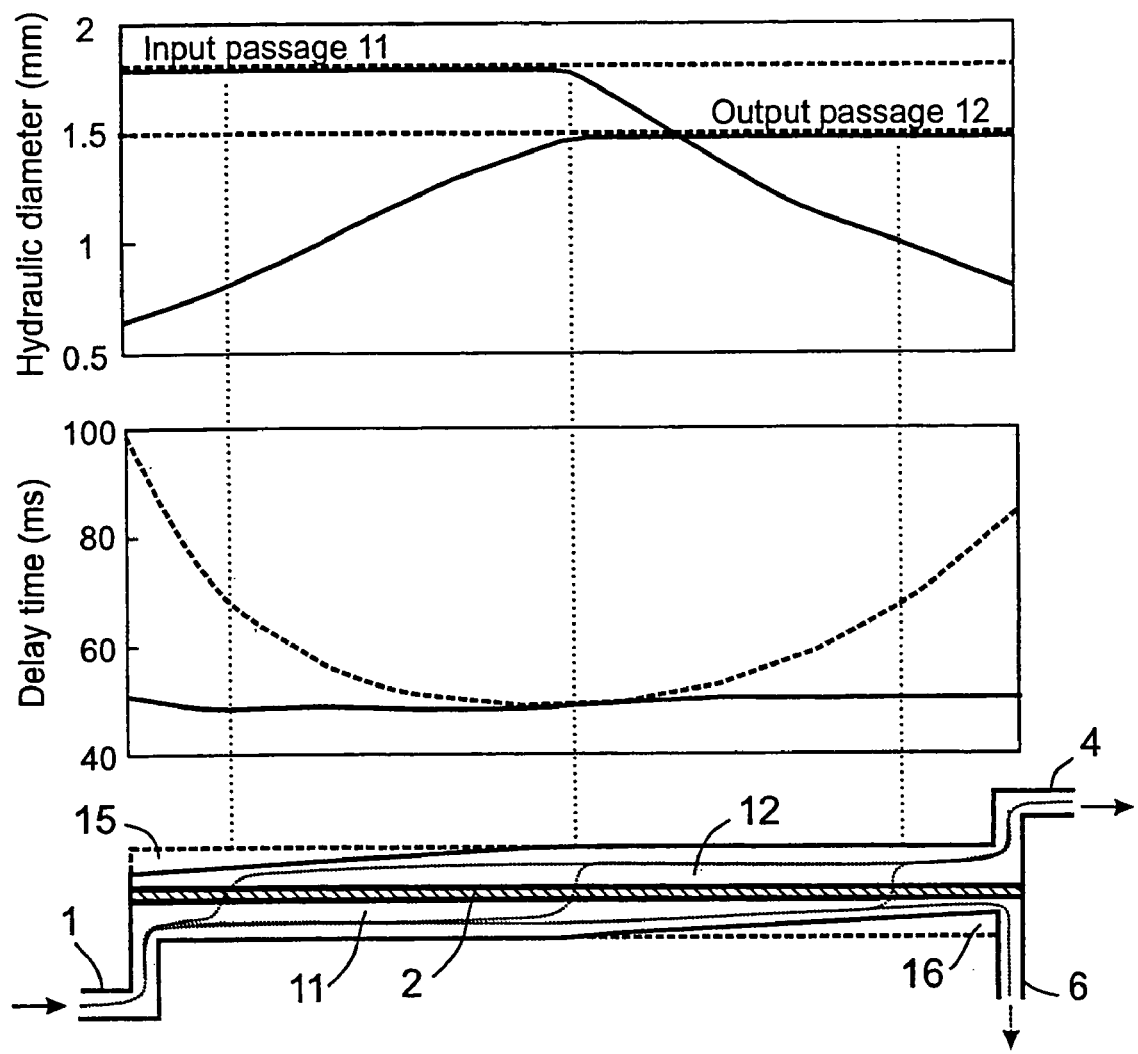
FIG. 4 shows how the parameters of one embodiment are changed compared to the prior art when using a modified embodiment according to the invention.
Figure 9:
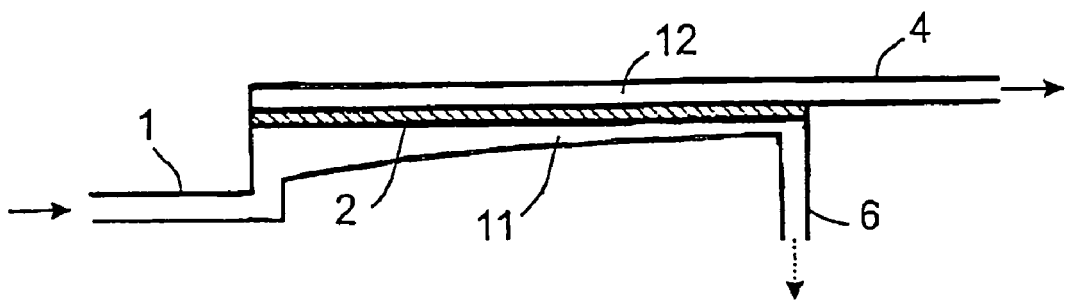
FIG. 9 shows a fifth embodiment of a liquid separator according to the invention.

In the same manner, the excessive delay time at the output end of the passage can be eliminated by suitably tapering the input passage 11 in the downstream direction at the output end 16. This is also shown in FIG. 4 using continuous lines, i.e. the input passage 11 has a narrowing profile extending along the input passage length and ending to the output end 16 of the input passage. The resulting smaller passage cross-section at the end 16 may affect the functioning of the liquid reception through the conduit 6. In case of problems the excessive delay time is anyhow smaller at this end of the passage so the tapering can be made smaller or the passage 11 can even be left unchanged. In fact, it is even possible to eliminate all the excessive delay time by tapering only the output passage 12. Its output end would then have to be tapered to a larger diameter than that of the unmodified passage in FIG. 4. Similarly, even if it might be less favorable, a reduction or elimination of the excessive delay time is also possible by tapering only the input passage 11 and leaving the output passage 12 unchanged. This is shown in FIG. 9. The tapered profile is normally thought of as being a lateral section along the passage so that the height of the passage is modified. However, it is also possible to modify the width of the passage in a section parallel to the filter 2. Since this may increase the flow resistance it is normally preferable to modify only the height of the passage. The amount of tapering depends on the flow configuration. According to FIG. 4 it can be seen that the passages are tapered to about half of their hydraulic diameters. This means that the cross-sectional area of the passage has been reduced to about one fourth of its unmodified value. Although even a small amount of tapering is beneficial it is preferable that the cross-sectional area of the passage changes at least by a factor of two. For the output passage this means that the cross-sectional area widens by a factor of at least two. The opposite is true for the input passage if applied. If the passage is tapered to zero the limits of tapering are difficult to define using area factors. In such a case the angle of widening is more well-defined. The upper limit of this angle depends on the length of the passage but is in practice about 30 degrees or preferably less than 20 degrees. Similarly, the lower limit is about 0.5 degrees or preferably more than 3 degrees. The angle may change along the passage as indicated e.g. in FIG. 9.

Figure 5:
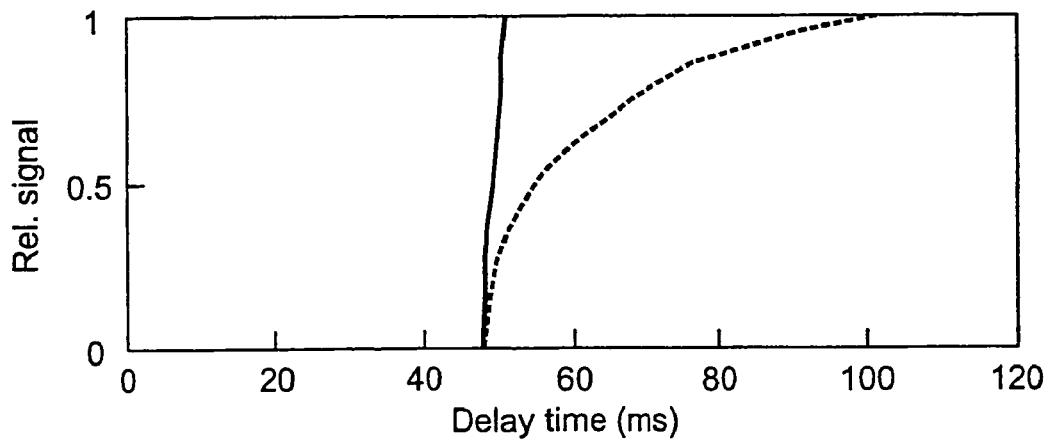
FIG. 5 shows the calculated delay time for a gas front after passing a liquid separator.
Figure 6:
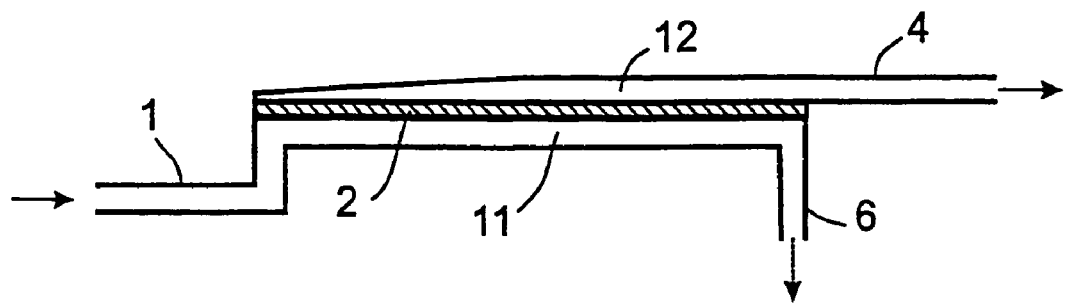
FIG. 6 shows a second embodiment of a liquid separator according to the invention.

From the data in FIG. 4 it is possible to estimate the response time of a gas front flowing through the liquid separator. This is shown in FIG. 5. The relative signal is representative of the output from the gas sensor 5 measuring the change in a gas constituent, supposing no other delay factors are present. Again, the dashed line and the continuous line refer to the prior art and the modified solution according to the invention, respectively. There is a delay time of about 50 ms before the gas front starts to reach the output of the liquid separator. The following increase of the signal is a measure of how fast the reaction to a change in the gas front can be. It is assumed that the gas front incident on the liquid separator is a step change in gas constituent, e.g. from 0% $CO_2$ to 5% $CO_2$ The rise time is defined as the signal change from 10% to 90% of the maximum value. For the prior art the rise time is about 40 ms whereas it is reduced to only about 1 ms for the modified version. The initial delay time of 50 ms is related to the flow velocity and can be reduced using a narrower or a shorter passage. However, the induced rise time contribution can almost be eliminated by suitably tapering one or both passages.

The delay time of the gas front is dependent of the gas flow velocity as mentioned above. In the unmodified channel the flow velocity will decrease along the input passage. Similarly, the flow velocity will increase along the output passage as more and more gas penetrates the gas permeable filter 2. Both passages will thus create excessive delay. Ideally, by modifying one or both passages in such a manner that the flow velocity at any specific position along the passage is approximately similar in both input and output passages each gas molecule suffers the same delay independently of where it went through the filter 2, i.e. the gas transit time is the same for all measured gas molecules. If the output end of the input passage is tapered as described in FIG. 4 the velocity along the passage first drops like in the unmodified case and then starts to rise again because of the tapering. The optimal modification would make the velocity profile along the second half of the input passage equal to the velocity profile of the second half of the output passage. Further, as a consequence of an optimal modification of the upper passage the velocity profile along the input end of the output channel is approximately similar to the velocity profile of the input end of the input passage the complete velocity profiles along the two passages should in other words preferably be identical. This can also be achieved by modifying only one of the passages as shown in FIG. 9. However, the diameter of the passage may then have to be made excessively large with consequential influence on the rise time. Also, the total delay time of the gas in the liquid separator increases compared to the case when both passages are modified, even if the rise time is equally well optimized in both cases. The optimal way of modifying the passages is to speed up the flow in portions where it is too slow. In FIG. 9 the flow velocity has been slowed down at the input end of the input passage to match the flow velocity at the input end of the output passage and speeded up at the output end of the input passage to match the velocity at the output end of the output passage. The first part of this procedure results in an increase of the total delay time of the liquid separator. In practice a less optimal modification may, however, be justified and sufficient considering other sources of delay in the gas analyzer.

The modification of the input and output passages can be accomplished in different ways. At least one passage, preferably the output passage should be tapered as is shown in FIG. 6. Here the input passage is left unchanged and the side flow through conduit 6 reduces the contribution to the rise time measured by the gas sensor 5. In this embodiment the output conduit 4 is connected to the output passage 12 without bends. This is an advantageous solution if it is mechanically possible to implement because a bend always has a contribution to the rise time of the system. In practice, the bend angle should preferably stay below about 30 degrees, the lower most preferable limit being above 0.5 degrees or, still better, no bend at all. For the same reasons the radius of curvature of the passage 11 and 12 should be more than about 5 times or preferably more than 10 times the hydraulic diameter of the unmodified passage. The most preferable factor would be very large, meaning a straight passage as in FIGS. 4-8. The tapered part of the output passage 12 is preferably tapered only in one dimension but it can also be tapered in two dimensions. If the contact area with the hydrophobic filter 2 is to be held unchanged, the height of the passage is modified like in the described embodiments. The important thing is that the hydraulic diameter is tapered.

Figure 7:
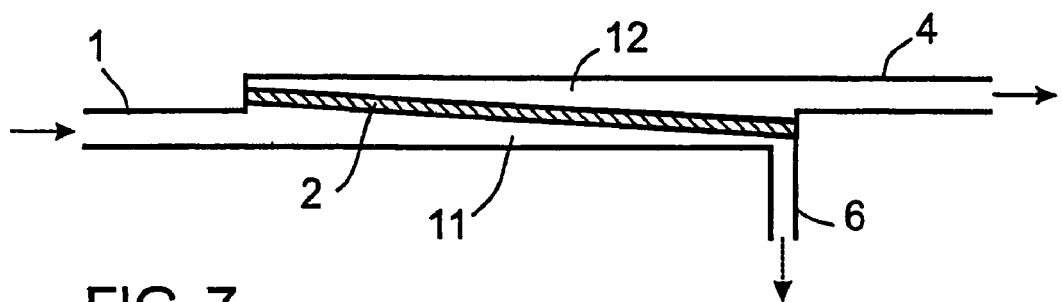
FIG. 7 shows a third embodiment of a liquid separator according to the invention.

The tapering can also be accomplished differently. In FIG. 7 the hydrophobic filter 2 has been mounted in a tilted position between the passages 11 and 12, i.e. the wall formed by the filter 2 made of gas permeable and liquid impermeable material is positioned in angular position with respect to the longitudinal directions of the input and output passages. This positioning automatically tapers the two passages along their whole length as can be seen in FIG. 7. Together with the straight connections this embodiment is close to an optimal solution.

Figure 8:
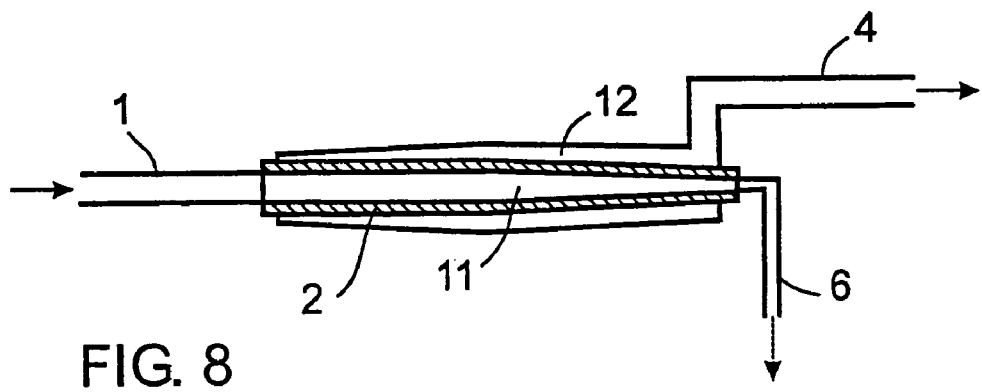
FIG. 8 shows a fourth embodiment of a liquid separator according to the invention.

In case the input passage 11 and output passage 12 are concentric tubes the tapered solution can be constructed like in the embodiment of FIG. 8. The solution needs a hydrophobic filter 2 with a conical surface shape having a conical form narrowing towards the output ends of the input and output passages 11, 12. Such a component may have to be specially made, but the solution has the advantage of a large contact area between the two passages like in the prior art embodiment of FIG. 2.

The velocity profile along the passages obviously depends on the specific modification of the passages. If e.g. the passage is tapered along its whole length like in FIG. 7 the gas flow velocity may even be constant along the passage. However, for an ideal solution it is sufficient that the velocity profiles along both passages are identical. As mentioned earlier, to make the total delay time as short as possible it is advantageous to increase the flow velocity at positions where it normally is slowed down, e.g. at the output end of the input passage and at the input end of the output passage. This is equivalent to tapering the passages to a smaller dimension at those positions.

The invention is by no means limited to the embodiments mentioned above but different details of the invention can be varied within the scope of the annexed claims.

The invention claimed is:

1. A liquid separator for removing liquid from a gas to be analyzed in a gas analyzer, said liquid separator comprising:
   an input passage having an input end to which a gas sample containing liquid is supplied, the input passage having an output end;
   an output passage having a first end and a second, output end; and
   a wall formed of a gas permeable and liquid impermeable material separating the input passage and the output passage in a region lying between the ends of the passages and along which region the passages lie on opposite sides of said wall, a first portion of the gas passing, in said region, through said wall from the input passage to the output passage for discharge from the output end of the output passage as the gas to be analyzed, a second portion of the gas sample and the liquid remaining in the input passage for discharge from the output end of the input passage;
   the output passage being formed such that the cross sectional area of the output passage taken generally transverse to a flow direction in the output passage increases in a tapered manner along the flow direction toward the output end of the output passage in at least a portion of the region along the passages in which the passages lie on opposite sides of said wall, the tapering being in an amount that causes the flow of gas along the passages to generate similar gas velocity profiles along the input and output passages.

2. The liquid separator of claim 1 wherein a tapered portion of the output passage extends over at least about half of the output passage length along said region.

3. The liquid separator of claim 2 wherein the input passage is formed such that the cross sectional area of the input passage taken generally transverse to a flow direction in the input passage decreases in a tapered manner along the flow direction toward the output end of the input passage in at least a portion of the region along the passages.

4. The liquid separator of claim 3 wherein the tapered portion of the input passage extends over at least about half of the input passage length in said region.

5. The liquid separator of claim 1 wherein the input passage is formed such that the cross sectional area of the input passage taken generally transverse to a flow direction in the input passage decreases in a tapered manner along the flow direction toward the output end of the input passage in at least a portion of the region along the passages.

6. The liquid separator of claim 5 wherein a tapered portion of the input passage extends over at least about half of the input passage length in said region.

7. The liquid separator of claim 6 wherein the input passage and the output passage are concentric tubular passages separated from each other by a tubular and cone shaped wall formed of a gas permeable and liquid impermeable material, the cone shaped wall tapering toward the output ends of the passages along said region.

8. The liquid separator of claim 5 wherein the cross sectional area profiles of the input and output passages are formed by positioning said wall separating the input and output passages in an angular position with respect to longitudinal flow directions of the input and output passages.

9. The liquid separator of claim 3 wherein a vacuum means is connectable to the output end of the output passage by using a conduit connected without bends to the output end of the output passage.

10. The liquid separator of claim 5 wherein the input passage and the output passage are concentric tubular passages separated from each other by a tubular and cone shaped wall formed of a gas permeable and liquid impermeable material, the cone shaped wall tapering toward the output ends of the passages along said region.

11. The liquid separator of claim 5 Wherein said output passage and said input passage are formed such that the cross sectional area increase in the former and the cross sectional area decrease in the latter cause similar gas velocity profiles along the passages.

12. The liquid separator of claim 1 wherein a vacuum means is connectable to the output end of the output passage by using a conduit connected without bends to the output end of the output passage.

13. The liquid separator of claim 1 wherein the input passage and the output passage are concentric tubular passages separated from each other by a tubular and cone shaped wall formed of a gas permeable and liquid impermeable material, the cone shaped wall tapering toward the output ends of the passages along said region.

14. The liquid separator of claim 1 wherein the tapering angle of the output passage is between the values 30 degrees and 0.5 degrees.

15. The liquid separator of claim 14 wherein the tapering angle of the output passage is more than 3 degrees but less than 20 degrees.

16. The liquid separator of claim 1 wherein the liquid separator includes a liquid receiving means, which is connected to the output end of the input passage for receiving the second portion of the gas and the liquid in the liquid receiving means.

17. A liquid separator for removing liquid from a gas to be analyzed in a gas analyzer, said liquid separator comprising:
an input passage having an input end to which a gas sample containing liquid is supplied, the input passage forming a gas flow passage in said separator and having an output end;
an output passage having a first end and a second, output end; and
a wall formed of a gas permeable and liquid impermeable material separating the input passage and the output passage in a region lying between the ends of the passages and along which region the passages lie on opposite sides of said wall, a first portion of the gas passing, in said region, through said wall from the input passage to the output passage for discharge from the output end of the output passage as the gas to be analyzed, a second portion of the gas sample and the liquid remaining in the input passage for discharge from the output end of the input passage;
the input passage and output passages having cross sectional areas generally transverse to a flow direction in the passages, the input passage being formed such that the cross sectional area of the input passage taken generally transverse to a flow direction in the input passage decreases in a tapered manner along the flow direction toward the output end of the input passage in at least a portion of the region along the passages in which the passages lie on opposite sides of said wall and adjacent said output end of said input passage, the cross sectional area of the input passage adjacent the input end of the input passage being greater than the cross sectional area of the output passage adjacent its input end by amount that causes the flow of gas along the passages to generate similar gas velocity profiles along the input and output passages.

18. The liquid separator of claim 17 wherein a tapered portion of the input passage extends over at least about half of the input passage length in said region.

19. The liquid separator of claim 17 wherein the tapering angle of the input passage is between the values 30 degrees and 0.5 degrees.

20. The liquid separator of claim 19 wherein the tapering angle of the input passage is more than 3 degrees but less than 20 degrees.

21. The liquid separator of claim 17 wherein the liquid separator includes a liquid receiving means, which is connected to the output end of the input passage for receiving the second portion of the gas and the liquid in the liquid receiving means.

22. A method for separating a small quantity of liquid from a gas stream to provide a large volume of gas from which the liquid has been separated, the gas stream intermittently containing a quantity of gas of interest to be analyzed in a gas analyzer, the separation being carried out in a manner that minimizes alteration of a response time of the gas analyzer, said method comprising the steps of:
providing the gas stream containing the small quantity of liquid and the intermittently appearing gas quantity of interest to an input end of an input passage of a separator; and
dividing the gas stream into two parts by using the input passage having an input end receiving the gas stream, the input passage having an output end; an output passage of the separator having a first end and a second, output end; and a gas permeable and liquid impermeable wall separating said two passages in a region in which the passages lie on opposite sides of the wall, a major part of the gas stream passing from the input passage through the wall to the output passage for supply to a gas analyzer at the output end of the output passage, a minor part of the gas stream, as well as the liquid, remaining in the input passage for discharge at the output end of the input passage;
the passages being so formed that the cross sectional areas of the input and output passages generally transverse to flow directions in the passages are varied such that the profile of the gas velocity along at least a portion of the output passage and the profile of the gas velocity along at least a corresponding portion of the input passage are approximately similar, the similar gas velocity profiles in the passages causing the gas quantity of interest to be analyzed to be presented to the gas analyzer in a form that minimizes alteration of the response time of the gas analyzer to the intermittent gas quantity of interest to be analyzed.

23. The method of claim 22 wherein the profile of the gas velocity along an input end portion of the output passage is approximately similar to the profile of the gas velocity along an input end portion of the input passage.

24. The method of claim 22 wherein the profile of the gas velocity along an output end portion of the input passage is approximately similar to the profile of the gas velocity along an output end portion of the output passage.

* * * * *